(12) United States Patent
Johnson (10) Patent No.: US 8,192,763 B2
(45) Date of Patent: Jun. 5, 2012

(54) PROCESSED ECM MATERIALS WITH ENHANCED COMPONENT PROFILES

(75) Inventor: Chad E. Johnson, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 955 days.

(21) Appl. No.: 12/178,321

(22) Filed: Jul. 23, 2008

(65) Prior Publication Data

US 2008/0286268 A1 Nov. 20, 2008

Related U.S. Application Data

(63) Continuation of application No. PCT/US2007/082238, filed on Oct. 23, 2007.

(60) Provisional application No. 60/853,584, filed on Oct. 23, 2006.

(51) Int. Cl.
*A61K 35/12* (2006.01)
*A61K 35/38* (2006.01)
*A61K 38/39* (2006.01)

(52) U.S. Cl. ........................................ 424/551; 424/423

(58) Field of Classification Search .................. 424/423, 424/551; 514/2, 21
See application file for complete search history.

(56) References Cited

U.S. PATENT DOCUMENTS

| | | | |
|---|---|---|---|
| 2,127,903 A | 8/1938 | Bowen | |
| 2,167,251 A | 7/1939 | Rogers | |
| 3,272,204 A | 9/1966 | Artandi et al. | |
| 3,649,163 A | 3/1972 | McCusker | |
| 4,321,914 A | 3/1982 | Begovac | |
| 4,361,552 A | 11/1982 | Baur, Jr. | |
| 4,781,176 A | 11/1988 | Ravo | |
| 4,801,299 A | 1/1989 | Brendel et al. | |
| 4,902,508 A | 2/1990 | Badylak et al. | |
| 4,956,178 A | 9/1990 | Badylak et al. | |
| 4,969,902 A | 11/1990 | Ravo | |
| 5,269,774 A | 12/1993 | Gray | |
| 5,275,826 A | 1/1994 | Badylak et al. | |
| 5,281,422 A | 1/1994 | Badylak et al. | |
| 5,336,616 A | 8/1994 | Livesey et al. | |
| 5,516,533 A | 5/1996 | Badylak et al. | |
| 5,554,389 A | 9/1996 | Badylak et al. | |
| 5,641,518 A | 6/1997 | Badylak et al. | |
| 5,645,860 A | 7/1997 | Knapp, Jr. et al. | |
| 5,711,969 A | 1/1998 | Patel et al. | |
| 5,755,791 A | 5/1998 | Whitson et al. | |
| 5,855,619 A | 1/1999 | Caplan et al. | |
| 5,955,110 A | 9/1999 | Patel et al. | |
| 5,968,096 A | 10/1999 | Whitson et al. | |
| 6,099,567 A | 8/2000 | Badylak et al. | |
| 6,206,931 B1 | 3/2001 | Cook et al. | |
| 6,371,992 B1 | 4/2002 | Tanagho et al. | |
| 6,375,989 B1 | 4/2002 | Badylak | |
| 6,379,710 B1 | 4/2002 | Badylak | |
| 6,475,232 B1 | 11/2002 | Babb et al. | |
| 6,576,618 B1 | 6/2003 | Herndon et al. | |
| 2003/0158607 A1 | 8/2003 | Carr, Jr. et al. | |
| 2004/0191226 A1 | 9/2004 | Badylak | |
| 2005/0021141 A1 | 1/2005 | Bleyer et al. | |
| 2005/0049638 A1 | 3/2005 | Mandelbaum | |
| 2005/0181016 A1 | 8/2005 | Freyman et al. | |

FOREIGN PATENT DOCUMENTS

| | | |
|---|---|---|
| WO | WO 96/24661 | 8/1996 |
| WO | WO 98/25964 | 6/1998 |
| WO | WO 99/62431 | 12/1999 |
| WO | WO 01/19285 | 3/2001 |
| WO | WO 02/40630 | 5/2002 |
| WO | WO 03/002165 | 1/2003 |
| WO | WO 2005/023321 | 3/2005 |
| WO | WO 2005/089411 | 9/2005 |
| WO | WO 2005/097219 | 10/2005 |

OTHER PUBLICATIONS

Abraham, Ginger A. et al., Evaluation of the porcine intestinal collagen layer as a biomaterial, J. Biomed Mater Res, 51, 442-452, 2000.

Clarke, Kevin M., et al., "Intestine Submucosa and Polypropylene Mesh for Abdominal Wall Repair in Dogs,", J. Surg. Res., 1996, 60:107-114.

Heeschen C., et al., "Nicotine stimulates angiogenesis and promotes tumor growth and atherosclerosis,", Nature Medicine 7 (2001), No. 7, 833-839.

Johnson C., et al., "Matrix Metalloproteinase-9 is Required for Adequate Angiogenic Revascularization of Ischemic Tissues: Potential Role in Capillary Branching," Circulation Research 94 (2004), No. 2, pp. 262-268.

Kropp et al., "Regenerative Urinary Bladder Augmentation Using Small Intestinal Submucosa: Urodynamic and Histopathologic Assessment in Long-Term Canine Bladder Augmenations," J. Urology, vol. 155, pp. 2098-2104, Jun. 1996.

Kropp, Bradley P. et al., "Experimental Assessment of Small Intestinal Submucosa as a Bladder Wall Substitute," Urology, 1995, 46:396-400.

Prevel, Christopher D. et al., "Small Intestinal Submucosa: Utilization for Repair of Rodent Abdominal Wall Defects", Ann. Plast. Surg., 1995, 35:374-388.

Rutchik, Jonathan S., M.D., MPH, Organic Solvents, Internet pages, www.emedicine.com/neuro/topic285.htm, last printed Apr. 27, 2006, 20 pages.

*Primary Examiner* — Ruth Davis

(74) *Attorney, Agent, or Firm* — Woodard, Emhardt, Moriarty, McNett & Henry LLP

(57) ABSTRACT

Described are medical graft materials and devices having improved properties relating to their component profiles.

31 Claims, 5 Drawing Sheets

PROCESSED ECM MATERIALS WITH ENHANCED COMPONENT PROFILES

REFERENCE TO RELATED APPLICATIONS

The present application is a continuation of International Application No. PCT/US2007/082238 filed Oct. 23, 2007, entitled "PROCESSED ECM MATERIALS WITH ENHANCED COMPONENT PROFILES" which claims the benefit of U.S. Provisional Patent Application Ser. No. 60/853,584 filed Oct. 23, 2006, entitled "PROCESSED ECM MATERIALS WITH ENHANCED COMPONENT PROFILES" both of which are hereby incorporated by reference in their entirety.

BACKGROUND

The present invention relates generally to medical graft materials and, in particular, to medical graft materials derived from tissue materials.

A variety of processed extracellular matrix (ECM) materials have been proposed for use in medical grafting, cell culture, and other related applications. For instance, medical grafts and cell culture materials containing submucosa derived from small intestine, stomach or urinary bladder tissues, have been proposed. See, e.g., U.S. Pat. Nos. 4,902,508, 4,956,178, 5,281,422, 5,554,389, 6,099,567 and 6,206,931. In addition, Cook Biotech Incorporated, West Lafayette, Ind., currently manufactures a variety of medical products based upon small intestinal submucosa under the trademarks SURGISIS®, STRATASIS® and OASIS®.

Medical materials derived from liver basement membrane have also been proposed, for example in U.S. Pat. No. 6,379,710. As well, ECM materials derived from amnion (see e.g. U.S. Pat. Nos. 4,361,552 and 6,576,618) and from renal capsule membrane (see International PCT Patent Application No. WO 03/002165 published Jan. 9, 2003) have been proposed for medical and/or cell culture applications.

Attempts have been made to provide a processed ECM material that retains medically significant substances other than collagen. However, in order to prepare a processed ECM in which undesired components have been removed, the material is typically subjected to a battery of manipulations, which can have undesirable consequences to the desirable components contained within the material. For example, submucosa and other ECM materials have been shown to include a variety of desirable components other than collagen that can contribute to the bioactivity of the materials and to their value in medical grafting and other uses. As examples, ECM materials can include growth factors, cell adhesion proteins, and proteoglycans that can be beneficial when retained in the processed ECM. However, it is difficult to selectively retain these components while removing high levels of undesired components in preparing a medically acceptable graft.

Needs remain for biomaterials that not only possess the necessary physical properties and high levels of biocompatibility and sterility, but also the desired levels of beneficial components. Methods for preparing and using these materials, as well as medical devices formed from these materials are also needed. The present invention addresses these needs.

SUMMARY

In one aspect, the present invention provides a medical graft material including a processed extracellular matrix (ECM) material. The ECM material retains collagen and non-collagen components, and desirably exhibits an angiogenic character. At the same time, the ECM material has low levels of undesired components such as native lipids, nucleic acids (e.g. DNA), and/or immunoglobulin A (IgA) components. In preferred embodiments, the ECM material includes submucosa.

In one embodiment, the present invention provides a medical graft material including a sterile, decellularized extracellular matrix (ECM) material. The ECM material includes native fibroblast growth factor-2 (FGF-2), and native immunoglobulin A (IgA) at a level of no greater than 20 µg/g. In some forms, the material can have a lipid content of no greater than about 4%. In preferred embodiments, the isolated ECM material includes submucosa and has a native IgA at a level of no greater than 5 µg/g and a native lipid content of no greater than about 3%.

In yet another aspect, the present invention provides a medical graft material including a sterile, decellularized extracellular matrix (ECM) material. The ECM material has a native FGF-2 content of at least about 10 ng/g and at least one of, and in certain forms each of (i) native IgA at a level of no greater than about 20 µg/g; (ii) native lipids at a level of no greater than about 4% by weight; (iii) native hyaluronic acid at a level of at least about 50 µg/g; and (iv) native sulfated glycosaminoglycan at a level of at least about 500 µg/g. In certain preferred embodiments, the ECM material includes submucosa. In additional forms, the ECM material has a native IgA at a level of no greater than about 5 µg/g and a native lipid content of no greater than about 3% by weight.

Further provided by the invention is a method for treating a patient. The method includes grafting the patient with a medical graft material of the invention.

The present invention further provides a method for preparing a medical graft material. The method comprises providing a starting extracellular matrix (ECM) material. The starting ECM material is treated to decrease the lipid, nucleic acid and/or IgA and/or other immunoglobulin content of the material while the material retains a significant level of growth factor(s), proteoglycans, and/or glycosaminoglycans. In certain embodiments, the method includes treating the starting ECM material with a dilute ionic detergent solution to disrupt cell and nuclear membranes, and with a basic solution to solubilize and remove DNA and other nucleic acid materials. The method can additionally include treating the ECM material with an organic solvent to remove lipids from the material, and/or with an oxidizing disinfectant solution, e.g. containing a peroxy compound, to disinfect the material. The ECM material is preferably rinsed to remove residues left by these solutions.

Medical graft materials of the invention can be provided in a wide variety of forms. For example, a medical graft material can be provided as one or more sheets, a paste, a sponge, a non-gelled aqueous solution, a powder, or a gel. Combinations of these forms are also contemplated.

The various forms of a medical graft material can be used in a wide variety of medical (including veterinary) applications. Examples include the repair or reconstruction of tissue, such as nervous tissue, dermal tissue (e.g. in wound care), cardiovascular tissue (including vascular tissue and cardiac tissue), pericardial tissue, muscle tissue, bladder tissue, ocular tissue, periodontal tissue, bone, connective tissue such as tendons or ligaments, and others.

Additional embodiments as well as features and advantages of the invention will be apparent from the descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations and further modifications in the described embodiments, and such further applications of the principles of the invention as illustrated herein being contemplated as would normally occur to one skilled in the art to which the invention relates.

As disclosed above, in one aspect the invention provides extracellular matrix graft materials having unique component profiles that are low in undesired components while retaining significant levels of desired components. These unique materials can be prepared by processing methods that comprise treating a relatively impure ECM starting material to decrease the content of the undesired components, such as nucleic acid, lipids and/or immunoglobulins such as IgA, while retaining substantial levels of desired components such as growth factor(s), proteoglycans and/or glycosaminoglycans (GAGs). Typically, the ECM starting material will be treated with a mild detergent solution, such as an ionic or nonionic detergent solution. The low concentration of detergent enables a retention of a substantial level of desired components, such as those as noted above. In certain modes of operation, the ECM material will be treated with an aqueous solution of sodium dodecyl sulfate (SDS) or another ionic or nonionic detergent at a detergent concentration of about 0.05% to about 1%, more preferably about 0.05% to about 0.3%. This treatment can be for a period of time effective to disrupt cell and nuclear membranes and to reduce the immunoglobulin (e.g. IgA) content of the ECM material, typically in the range of about 0.1 hour to about 10 hours, more typically in the range of about 0.5 hours to about 2 hours. Processing the isolated ECM material in this manner preferably disrupts cell and nuclear membranes and results in a material with a substantially reduced its IgA content, thus reducing the immunogenicity of the material. For example, a processed ECM material of the invention can have a native IgA content of no greater than about 20 µg/g. In preferred embodiments, an ECM material of the invention can have a native IgA content of no greater than 15 µg/g, no greater than 10 µg/g, or even no greater than 5 µg/g. In certain embodiments, the processed ECM material includes essentially no native IgA. By "essentially no IgA" is meant that the isolated ECM material includes IgA below detectable levels. Means for detecting IgA are well known in the art and include, for example, enzyme-linked immunosorbent assay (ELISA). It will be understood in this regard that ECM materials obtained from different sources may have differing immunoglobulins that predominate in the tissue. It is expected that the processing techniques disclosed herein will be effective to reduce the content of ECM materials in other immunoglobulins, including those that predominate in the source tissue. Accordingly, other aspects of the invention relate to the isolation of an ECM material that has substantially reduced levels (e.g. less than about 20 µg/g) of (i) the predominant immunoglobulin in the source tissue, or (ii) the total immunoglobulin content (the sum of all immunoglobulins in the tissue).

In addition to treating an ECM material with a detergent medium, the ECM material can be contacted with other agents that participate in achieving the desired ECM component profile. For example, the ECM material can be treated with an aqueous medium, preferably basic, in which DNA is soluble. Such a medium can in certain forms have a pH in the range of above 7 to about 9, with pH's in the range of about 8 to about 8.5 proving particularly beneficial in some embodiments. The basic aqueous medium can include a buffer, desirably a biocompatible buffer such as tris(hydroxymethyl)aminomethane (TRIS), and/or a chelating agent such as ethylene diamine tetraacetic acid (EDTA). In one preferred form, the nucleic acid solubilizing medium is a TRIS-borate-EDTA (TBE) buffer solution. In another preferred form, the nucleic acid solubilizing medium is a solution of ammonium hydroxide. This treatment with a DNA solubilizing medium can be for a period of time effective to reduce the DNA content of the ECM material, typically in the range of about 0.1 hour to about 10 hours, more typically in the range of about 0.5 hours to about 2 hours.

In addition to treatment with detergent and DNA-solubilization media, methods of preparing medical graft materials of the invention can involve treatment with a liquid medium that results in a substantial reduction of the level of lipid components of the ECM material. For example, the resulting native lipid content of the ECM material can be reduced to no greater than about 4% in certain embodiments. This can be accomplished, for example, by a preparative process that involves a step of treating the ECM material with a liquid organic solvent in which the lipids are soluble. Suitable such organic solvents include for example water-miscible solvents, including polar organic solvents. These include low molecular weight (e.g. $C_1$ to $C_4$) alcohols, e.g. methanol, ethanol, isopropanol, and butanols, acetone, chloroform, and others. Additional organic solvents include nonpolar solvents such as hexane, benzene, toluene and the like. In more preferred embodiments, the processed ECM material will be processed to have a native lipid content no greater than about 3%, or no greater than about 2.5%. This treatment with a lipid-removing medium can be for a period of time effective to reduce the lipid content of the ECM material, typically in the range of about 0.1 hour to about 10 hours, more typically in the range of about 0.1 hours to about 1 hours. In certain embodiments, multiple (two or more) such treatments will be conducted. Additionally, treatment with the lipid-reducing medium as discussed above can be carried out before or after treatment with a detergent medium and/or aqueous (preferably basic) DNA-reducing medium as discussed above. In certain preferred embodiments, treatment with the lipid-reducing medium will occur before treatment with the detergent medium and/or the aqueous (preferably basic) medium.

The ECM material can also be treated with a disinfecting solution. The disinfecting solution can include a disinfecting agent such as an alcohol, a peroxy compound, or another oxidizing or non-oxidizing disinfectant. In certain forms, the disinfecting solution will be a peracetic acid solution having a peracetic acid concentration of about 0.1% to about 0.3%. Peracetic acid and other oxidizing disinfectant treatment solutions such as those described in U.S. Pat. No. 6,206,931 can be used, for example.

The ECM material also can be rinsed at various stages throughout its preparation (e.g., with tap water, high purity water or buffer) so as to remove introduced chemical residues that remain in or on the material. In preferred embodiments, at least about 90% of detergent residues are removed from the material. More preferably, at least about 95%, or at least about 97% of detergent residues are removed from the material.

Treatments with detergent, DNA-solubilizing, lipid-solubilizing, rinsing, and potentially other liquid media can be carried out in any suitable fashion and in any suitable order wherein the ECM material is contacted with the medium. For example, the ECM material can be soaked in the medium, potentially with agitation, for the duration of the treatment. Other contacting methods such as spraying or showering the ECM material with the medium can also be used. As well, the treatment(s) can be carried out at any suitable temperature. Temperatures of 0° C. to about 50° C. are preferred as they enable minimizing or avoiding substantial denaturing of the collagen and other desirable components of the ECM material. More preferably, the treatment temperature will be in the range of about 0° C. to about 37° C., and more typically in the range of about 20° C. to about 37° C. It will be understood, however, that other temperatures may be used within the broader aspects of the invention. In embodiments where a tubular or other closable structure is formed, the ECM material including a lumen can be clamped at one end to allow the lumen to be filled with medium and can be clamped at the other end to essentially close a proximal and distal end of the tubular ECM material. The tubular ECM material having a filled lumen can be submerged in a medium, which can be the same or different medium. In this way, each of the lumen and the outer surface of a tubular ECM material can be treated without necessarily requiring that the treatment medium diffuses or otherwise passes through the ECM material. This process can be repeated with any medium used herein, including any rinsing step.

Treatments such as those above, and/or other chemical and/or mechanical treatments, will decellularize the ECM tissue, desirably resulting in a processed ECM tissue that is free of viable cells derived from the source tissue. Acellular ECM material so obtained can, however, be used to culture or be seeded with cells in certain embodiments, for example certain of those described below.

Processed ECM materials of the invention can be derived from any suitable organ or other tissue source, desirably one containing significant collagenous connective tissue. Human or other animal tissue sources can be used. Non-human animal sources can be warm-blooded vertebrates, including mammals, with bovine, ovine, caprine, and porcine sources being suitable. Suitable ECM materials obtained from these tissue sources can include submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. It will be well understood that in isolating ECMs that include submucosa, some or all of the original submucosa from the source tissue may be retained, potentially along with materials derived from one or more adjacent tissue layers. Similar principles apply to other collagen-rich layers or other tissues named herein—the recovered ECM material may include some or all of the specified tissue originally present in the source tissue, and/or may remain connected to adjacent tissue(s) in the final processed ECM material.

Processed, naturally-derived ECM materials of the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive components, the ECM material can retain these components interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The processed ECM material of the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

It is advantageous to prepare bioremodelable ECM materials for the medical graft materials and methods of the present invention. Such materials that are bioremodelable and promote cellular invasion and ingrowth provide particular advantage. Bioremodelable materials may be used in this context to promote cellular growth within the site in which a medical graft material of the invention is implanted.

As noted above, the processed submucosal (submucosa-containing) ECM material and any other ECM material may retain any of a variety of growth factors or other beneficial bioactive components native to the source tissue. For example, the submucosa or other ECM can include one or more native growth factors such as basic fibroblast growth factor (FGF-2), transforming growth factor beta (TGF-beta), epidermal growth factor (EGF), connective tissue growth factor (CTGF), vascular endothelial growth factor (VEGF) and/or platelet derived growth factor (PDGF). As well, submucosa or other ECM used in the invention may include other biological materials such as proteoglycans and/or glycosaminoglycans, such as heparin, heparin sulfate, hyaluronic acid, fibronectin and the like. Thus, generally speaking, the processed ECM material will include at least one native bioactive component that induces, directly or indirectly, a cellular response such as a change in cell morphology, proliferation, growth, protein or gene expression.

In preferred embodiments, the processed ECM material will exhibit a component profile wherein the following non-collagen components are present in the stated amounts:

| Component | Preferred Range | More Preferred Range |
| --- | --- | --- |
| Lipid: | less than 5% | less than 3% |
| FGF-2: | greater than 2 ng/g | greater than 5 ng/g |
| IgA: | less than 5 µg/g | less than 1 µg/g |
| HA: | greater than 50 µg/g | greater than 100 µg/g |
| sGAG: | greater than 1000 µg/g | greater than 2000 µg/g |
| Visible nuclei | less than 200 per 0.263 mm$^2$ | less than 100 per 0.263 mm$^2$ |

Further, in addition to the retention of native bioactive components, non-native bioactive components such as those synthetically produced by recombinant technology or other methods, may be incorporated into the submucosal or other ECM material. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

A non-native bioactive component can be applied to a submucosa or other ECM tissue by any suitable means. Suitable means include, for example, spraying, impregnating, dipping, etc. The non-native bioactive component can be applied to the ECM tissue either before or after the material is affixed to an elongate member. Similarly, if other chemical or biological components are included in the ECM tissue, the non-native bioactive component can be applied either before, in conjunction with, or after these other components.

Processed submucosal or other ECM tissue of the invention preferably exhibits an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 2 µg/mg, more preferably less than about 1 µg/mg, and virus levels are preferably less than about 50 plaque forming units (PFU) per gram, more preferably less than about 5 PFU per gram.

In certain embodiments, endotoxin levels can be considered in relation to the surface area of one or more isolated, single sheets of an ECM material. In such instances, a sheet of ECM material can exhibit an endotoxin level of less than about 0.25 EU/cm$^2$. In preferred embodiments, a sheet of ECM material exhibits an endotoxin level of less than about 0.2 EU/cm$^2$, less than about 0.1 EU/cm$^2$, and even less than about 0.05/cm$^2$. In a most preferred embodiment, a sheet of ECM material exhibits an endotoxin level of less than about 0.025 EU/cm$^2$. Multilayer ECM structures including a plurality of bonded or otherwise coupled sheets of ECM material can exhibit similar endotoxin levels based on the surface area of the overall multilayer structure.

The processed ECM material of the invention can be packaged or otherwise stored in a dehydrated or hydrated state. Dehydration of a medical graft material of the invention can be achieved by any means known in the art. Preferably, dehydration is accomplished by either lyophilization or vacuum pressing, although other techniques, for example air drying, can also be used. When stored in a dry state, it will often be desirable to rehydrate the processed ECM material prior to use. In this regard, any suitable wetting medium can be used to rehydrate the medical material, including as examples water or buffered saline solutions.

In certain embodiments, the processed ECM material can be crosslinked. Increasing the amount (or number) of crosslinkages within the medical graft material or between two or more layers of the medical graft material can be used to enhance its strength. However, crosslinkages within the medical graft material may also effect its bioremodelability or other bioactive characteristics. Consequently, in certain embodiments, a bioremodelable ECM material will be provided that substantially retains its native level of crosslinking, or the amount and/or type of added crosslinks within the ECM material can be judiciously selected to retain the desired level of bioremodelability or other bioactive characteristic.

For use in the present invention, any introduced crosslinking of the processed ECM material may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acylazide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule. Preferably, a medical graft material is crosslinked with a crosslinking agent comprising transglutaminase.

Processed ECM materials of the invention can be manufactured into a variety of physical forms to suit a variety of medical applications. For example, an isolated ECM material can be provided as one or more sheets, a paste, a foam, a non-gelled aqueous solution, a powder, or a gel. Combinations of these forms are also contemplated. In this regard, the configuration of the ECM material may be attained before or after the ECM material has been processed as described herein. Further, an ECM composite material can be manufactured in larger, bulk dimensions, and then divided into smaller products. Moreover, the ECM material may provided in a naturally-derived layer form, or may itself be a manufactured article, such as a sponge or cast sheet, prepared from a naturally-derived ECM material.

Medical graft materials of the invention may be used in a wide variety of medical (including veterinary) applications. Examples include the repair or reconstruction of tissue, such as nervous tissue, dermal tissue such as in wound healing, e.g. application to external dermal wounds, including but not limited to ulcers (e.g. diabetic or other chronic ulcers), cardiovascular tissue (including vascular tissue and cardiac tissue), pericardial tissue, muscle tissue, ocular tissue, periodontal tissue, bone, connective tissue such as tendons or ligaments, in the treatment of gastrointestinal fistulae (e.g. processed into the form of a plug to occlude at least the primary opening of a fistula such as an anorectal, rectovaginal, or enterocutaneous fistula), and others.

In one embodiment, the processed ECM material is made into a fluidized composition, for instance using techniques as described in U.S. Pat. Nos. 5,275,826 and 5,516,533. In this regard, solutions or suspensions of the ECM material can be prepared by comminuting and/or digesting the material with a protease (e.g. trypsin or pepsin), for a period of time sufficient to solubilize the material and form substantially homogeneous solution. The ECM material is desirably comminuted by tearing, cutting, grinding, shearing or the like. Grinding the material in a frozen or freeze-dried state is advantageous, although good results can be obtained as well by subjecting a suspension of pieces of the material to treatment in a high speed blender and dewatering, if necessary, by centrifuging and decanting excess waste. The comminuted material can be dried, for example freeze dried, to form a powder. Thereafter, if desired, the powder can be hydrated, that is, combined with water or buffered saline and optionally other pharmaceutically acceptable excipients, to form a fluid tissue graft composition, e.g. having a viscosity of about 2 to about 300,000 cps at 25° C. The higher viscosity graft compositions can have a gel or paste consistency.

A fluidized ECM material of this invention finds use as an injectable heterograft for tissues, for example, bone or soft tissues, in need of repair or augmentation most typically to correct trauma or disease-induced tissue defects. The present fluidized compositions are also used advantageously as a filler for implant constructs comprising, for example, one or more sheets of a collagenous ECM material formed into sealed (sutured) pouches for use in cosmetic or trauma-treating surgical procedures.

In one illustrative preparation, an ECM material prepared as described herein is reduced to small pieces (e.g. by cutting) which are charged to a flat bottom stainless steel container. Liquid nitrogen is introduced into the container to freeze the specimens, which are then comminuted while in the frozen state to form a coarse powder. Such processing can be carried out, for example, with a manual arbor press with a cylindrical brass ingot placed on top of the frozen specimens. The ingot serves as an interface between the specimens and the arbor of the press. Liquid nitrogen can be added periodically to the specimens to keep them frozen.

Other methods for comminuting ECM material specimens can be utilized to produce a powder usable in accordance with the present invention. For example, ECM material specimens can be freeze-dried and then ground using a manual arbor press or other grinding means. Alternatively, ECM material can be processed in a high shear blender to produce, upon dewatering and drying, a powder.

Further grinding of the ECM material powder using a prechilled mortar and pestle can be used to produce consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

To prepare another preferred fluidized material, an ECM material powder can be sifted through a wire mesh, collected, and subjected to proteolytic digestion to form a substantially homogeneous solution. For example, the powder can be digested with 1 mg/ml of pepsin (Sigma Chemical Co., St. Louis Mo.) and 0.1 M acetic acid, adjusted to pH 2.5 with HCl, over a 48 hour period at room temperature. After this treatment, the reaction medium can be neutralized with sodium hydroxide (NaOH) to inactivate the peptic activity. The solubilized submucosa can then be concentrated by salt precipitation of the solution and separated for further purification and/or freeze drying to form a protease-solubilized collagenous ECM material in powder form.

Fluidized compositions of this invention find wide application in tissue replacement, augmentation, and/or repair. The fluidized compositions can be used to induce regrowth of natural connective tissue or bone in an area of an existent defect. By injecting an effective amount of a fluidized composition into the locale of a tissue defect or a wound in need of healing, one can readily take advantage of the biotropic properties of the collagenous ECM material.

In orthopedic applications, a medical graft material of the invention can be used to repair bone tissue, for instance using the general techniques described in U.S. Pat. No. 5,641,518. Thus, a powder form of the material can be implanted into a damaged or diseased bone region for repair. The powder can be used alone, or in combination with one or more additional bioactive agents such as physiologically compatible minerals, growth factors, antibiotics, chemotherapeutic agents, antigen, antibodies, enzymes and hormones. Preferably, the powder-form implant will be compressed into a predetermined, three-dimensional shape, which will be implanted into the bone region and will substantially retain its shape during replacement of the graft with endogenous tissues.

A processed ECM material of the invention can also be used as a cell growth substrate, illustratively in sheet, paste or gel form in combination with nutrients which support the growth of the subject cells, e.g. eukaryotic cells such as endothelial, fibroblastic, fetal skin, osteosarcoma, and adenocarcinoma cells (see, e.g. International PCT Application Publication No. WO 96/24661). In preferred forms, the substrate composition will support the proliferation and/or differentiation of mammalian cells, including human cells.

A processed ECM material of the invention can also be used in body wall repair, including for example in the repair of abdominal wall defects such as hernias, using techniques analogous to those described in *Ann. Plast. Surg.,* 1995, 35:374-380; and *J. Surg. Res.,* 1996, 60:107-114. In such applications, preferred medical graft materials of the invention promote favorable organization, vascularity and consistency in the remodeled tissue. In dermatological applications, a medical graft material of the invention can be used in the repair of partial or full thickness wounds and in dermal augmentation using general grafting techniques which are known to the art and literature (see, e.g. *Annals of Plastic Surgery* 1995, 35:381-388). In addition, in the area of burn treatment, it is generally known to provide a dermal substitute onto which cultured epidermal grafts (preferably cultured epidermal autografts, or CEA's) are transplanted. Such cultured grafts have typically involved transplanting keratinocytes and/or fibroblasts onto the dermal substitute. In accordance with the present invention, the medical graft material can be used as the dermal substitute, for example in sheet form, and the CEA accordingly transplanted onto the material. In one mode of practicing this aspect of the invention, keratinocytes can be transplanted, for example by seeding or transferring a keratinocyte sheet, onto the mucosal side of the submucosa. Fibroblasts can be transplanted also on the mucosal and/or on the opposite (abluminal) side of the submucosa.

The processed ECM material of the invention can also be used in tissue grafting in urogenital applications. For instance, the medical graft material can be used in urinary bladder repair to provide a scaffold for bladder regeneration, using techniques corresponding to those generally described in U.S. Pat. No. 5,645,860; *Urology,* 1995, 46:396-400; and *J. Urology,* 1996, 155:2098. In fluidized form, the inventive medical graft material can also find use in an endoscopic injection procedure to correct vesicureteral reflux. In such applications, an injection can be made, for instance in the area under the ureteral orifice of a patient, to induce smooth muscle growth and collagen formation at the injection site.

Generally, when configured for use as a tissue graft, the processed ECM material of the invention can include one or more sheets of ECM material that can be cut or otherwise configured to a desired size for its end use. The graft material is in many instances sized larger than the tissue defect to which it is applied. Sizing the medical graft material in this way allows for easy attachment to the surrounding tissue.

Once the sized ECM graft material has been placed on, in, or around the defect, the material can be attached to the surrounding tissue using any of several known suitable attachment means. Suitable attachment means include, for example, biocompatible adhesives (e.g., fibrin glue), stapling, suturing, and the like. Preferably, the medical graft material is attached to the surrounding tissue by sutures. There are a variety of synthetic materials currently available in the art for use as sutures. For example, sutures comprising Prolene™, Vicryl™, Mersilene™, Panacryl™, and Monocryl™, are contemplated for use in the invention. Other suture materials will be well known to those skilled in the art. The aforementioned materials therefore serve merely as examples and, consequently, are in no way limiting.

In other areas, medical graft materials formed with an ECM material of the present invention can be used in neurologic applications, for example in techniques requiring a dural substitute to repair defects due to trauma, tumor resection, or decompressive procedures.

In sheet form, a processed ECM medical graft material of the invention can be comprised of a single layer or multiple layers of material. Thus, in certain embodiments, a single isolated layer of ECM material or a multilaminate ECM construct can be used. Illustrative multilaminate ECM constructs for use in the invention may, for example, have from two to about ten isolated ECM layers laminated together.

Multilaminate ECM constructs for use in the invention can be prepared in any suitable fashion. In this regard, a variety of techniques for laminating ECM layers together can be used. These include, for instance, dehydrothermal bonding under heated, non-heated or lyophilization conditions, using adhesives, glues or other bonding agents, crosslinking with chemical agents or radiation (including UV radiation), or any combination of these with each other or other suitable methods. For additional information as to multilaminate ECM constructs that can be used in the invention, and methods for their preparation, reference may be made for example to U.S. Pat. Nos. 5,711,969, 5,755,791, 5,855,619, 5,955,110, 5,968,096, and to U.S. Patent Application Publication No. 20050049638.

Single layer ECM or multilaminate ECM constructs or other biocompatible materials used in the present invention can have or can lack perforations or slits in their structure, and in certain embodiments can have a meshed structure for example as described in U.S. Application Patent Publication No. 20050021141. Such mesh patterned structures can be used to provide an ECM or other implant segment that is highly deformable for use in the present invention.

In additional embodiments, processed ECM's of the invention can be subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a medical device. Illustratively, the expanded material can be enriched with bioactive components, dried, and/or molded, etc., in the formation of a graft construct of a desired shape or configuration. In certain embodiments, a medical graft material and/or device formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a tract within the patient.

Expanded ECM materials can be formed by the controlled contact of a processed ECM material as described above with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared medical graft material is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a medical graft material of the invention.

Medical graft materials of the invention also can be used in conjunction with one or more secondary components to construct a variety of medical devices. In certain embodiments, the processed ECM material is affixed to an expandable member, such as a self-expanding or forcibly expandable (e.g. balloon-expandable) stent or a frame. Such devices of the invention can be adapted for deployment within the cardiovascular system, including within an artery or vein. Certain devices are adapted as vascular valves, for example for percutaneous implantation within arteries, or within veins of the legs or feet to treat venous insufficiency.

Prosthetic valve devices made with processed ECM materials of the invention can be implanted into a bodily passage as frameless valve devices or, as noted above, the ECM material can be attached to an expandable frame. The ECM material can be used to form biocompatible coverings such as sleeves and/or to form leaflets or other valve structures (see, e.g. WO 99/62431 and WO 01/19285). In one mode of forming a valve structure, the processed ECM material can be attached to a stent in a fashion whereby it forms one, two, or more leaflets, cusps, pockets or similar structures that resist flow in one direction relative to another. In a specific application of such devices, such devices constructed as vascular valves are implanted to treat venous insufficiencies in humans, for example occurring in the legs.

Figure 1:
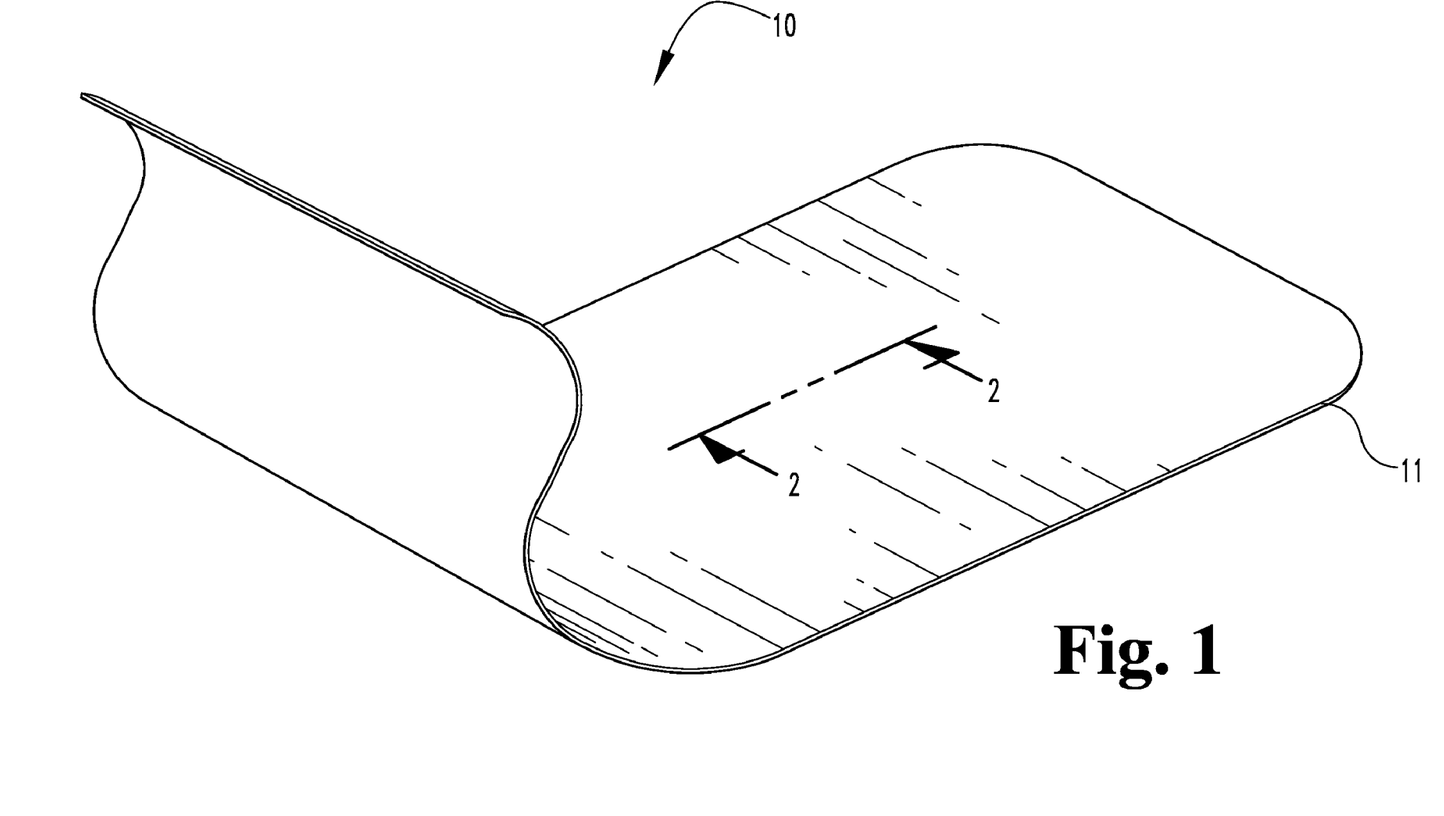
FIG. 1 depicts a medical graft material of the invention formed from a single layer of an extracellular matrix (ECM) material isolated from tissue of a warm blooded vertebrate.
Figure 2:
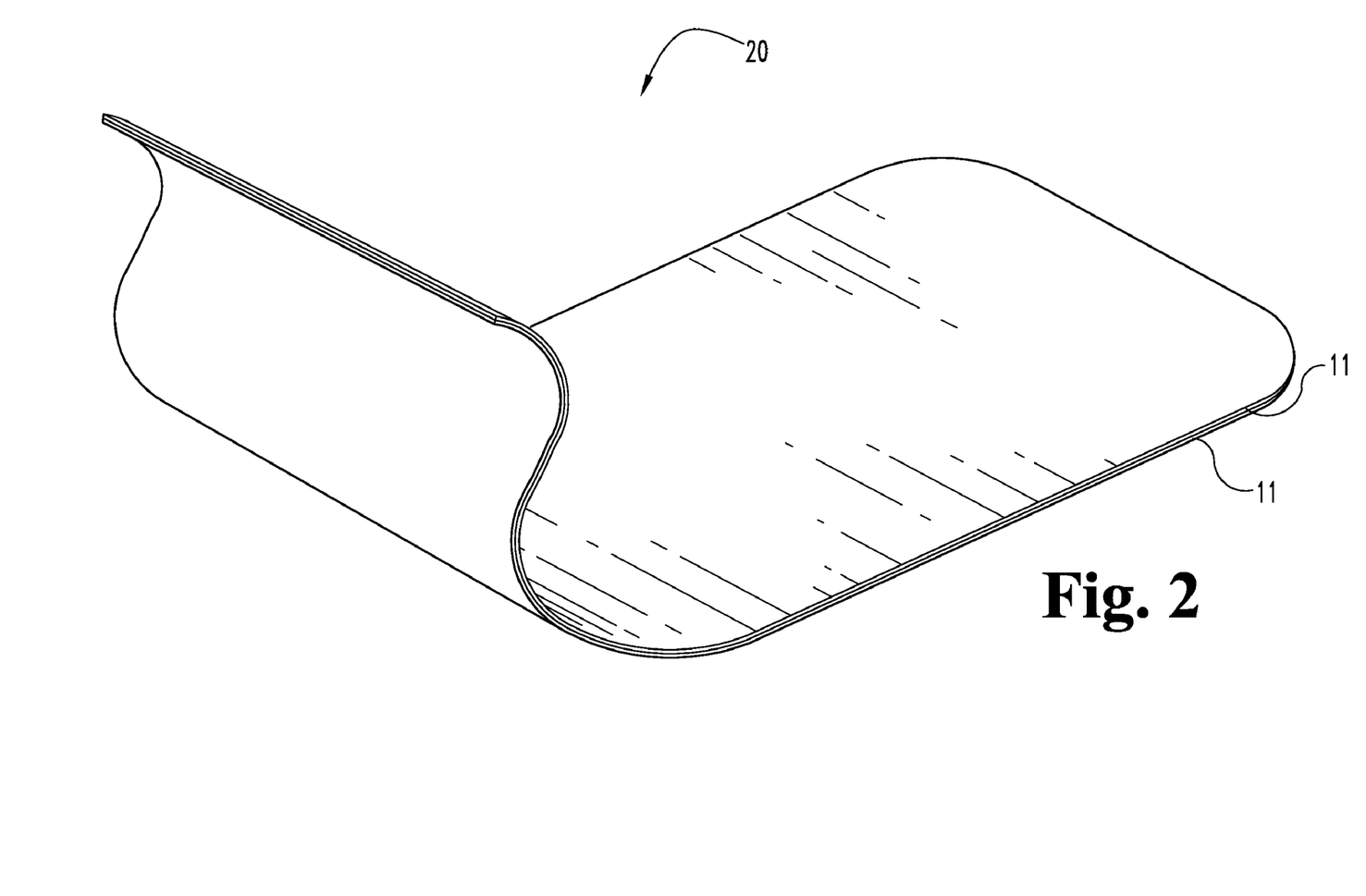
FIG. 2 depicts a medical graft material of the invention formed from two layers of an ECM material isolated from tissue of a warm blooded vertebrate.

With reference now to FIG. 1, depicted is a sheet-form medical graft 10 formed from a single layer of the inventive processed ECM material 11 derived from tissue of a warm blooded vertebrate. FIG. 2 illustrates a medical graft device 20 formed from two layers of the inventive processed ECM material 11. Sheet form medical graft devices as depicted in FIGS. 1 and 2 can be used in a variety of grafting applications as described herein, including without limitation in wound care and soft tissue support applications.

Figure 3:
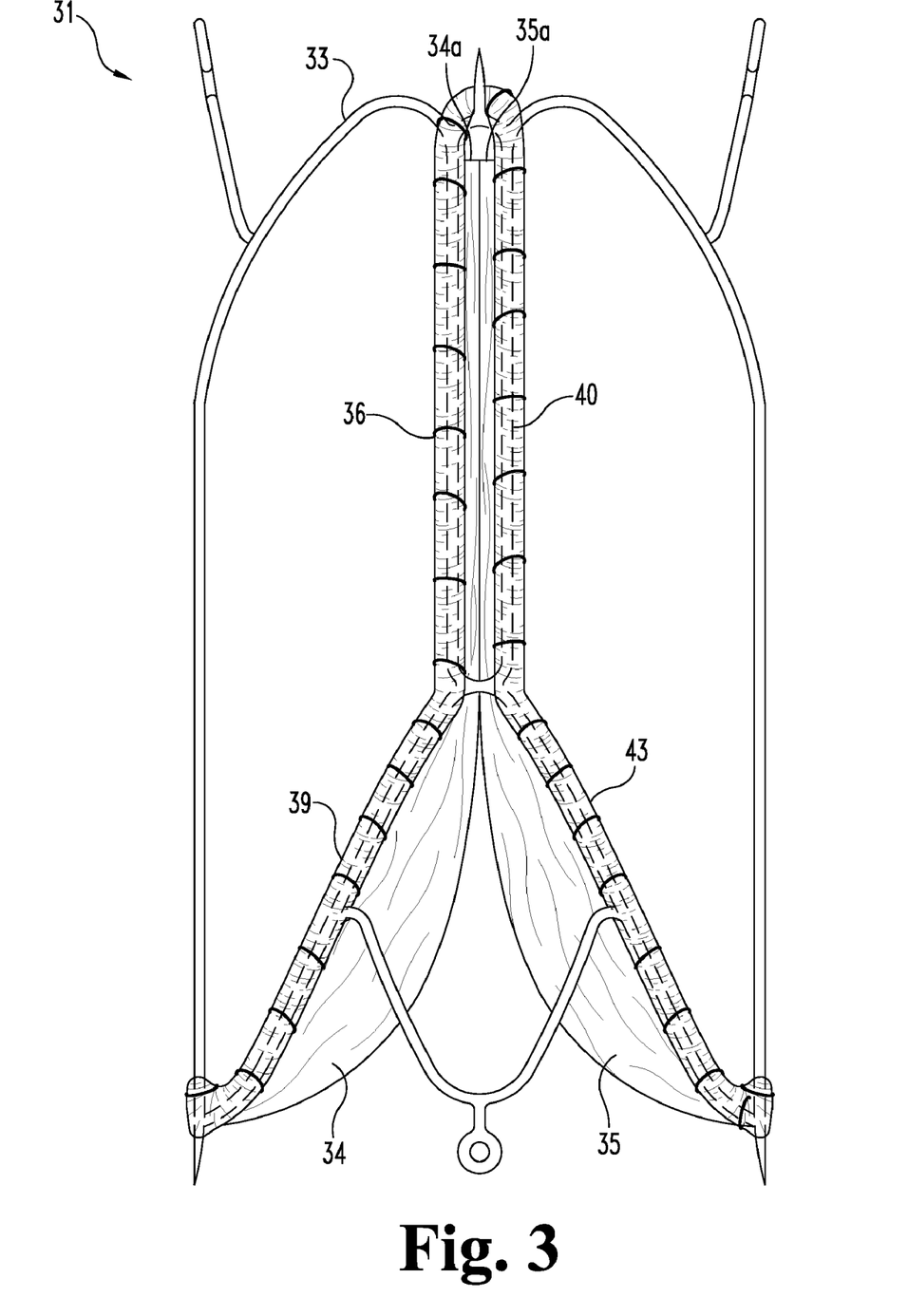
FIG. 3 provides a side view of one prosthetic valve device of the invention that includes an ECM material attached to a frame.
Figure 4:
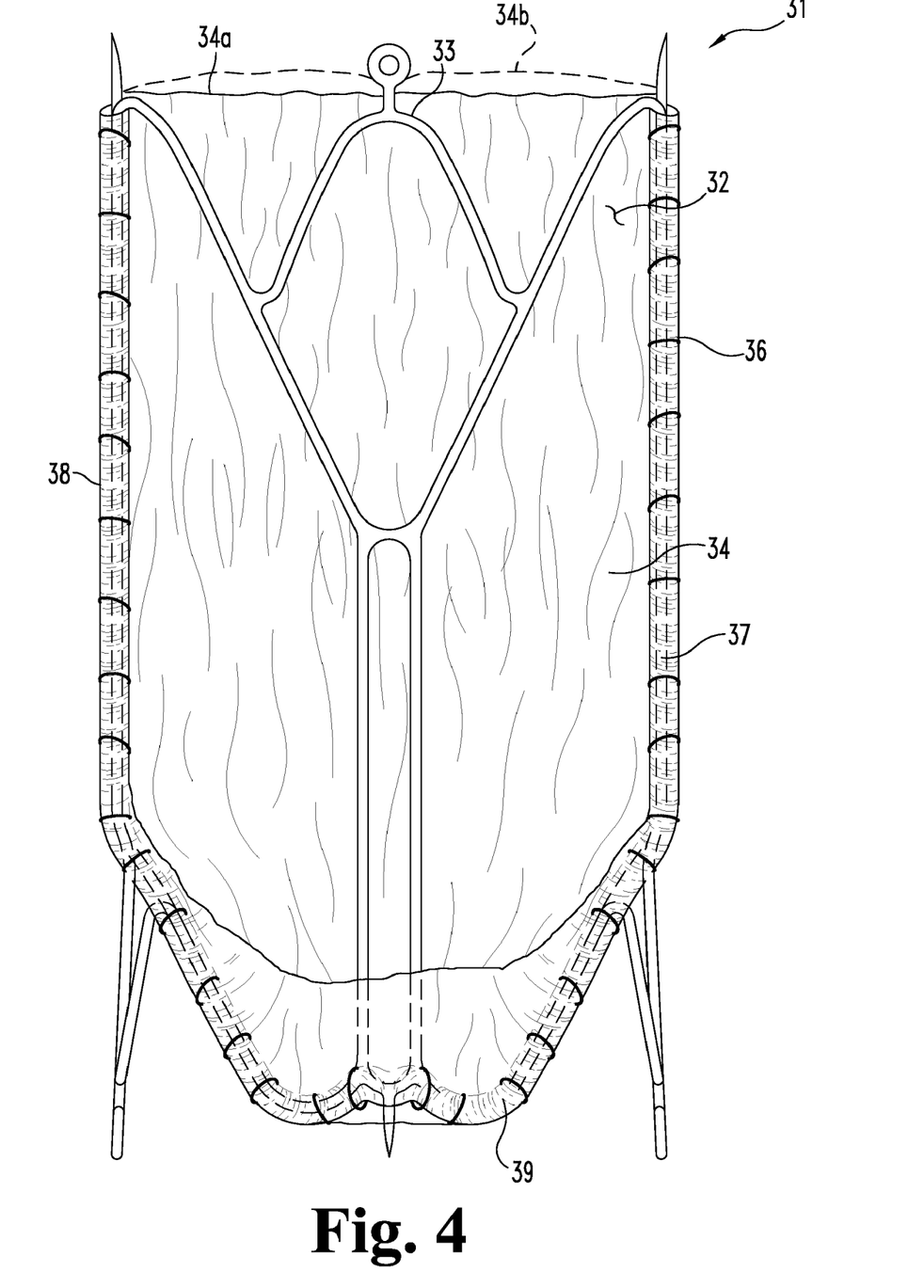
FIG. 4 provides a left side view of the prosthetic valve device depicted in FIG. 3.
Figure 5:
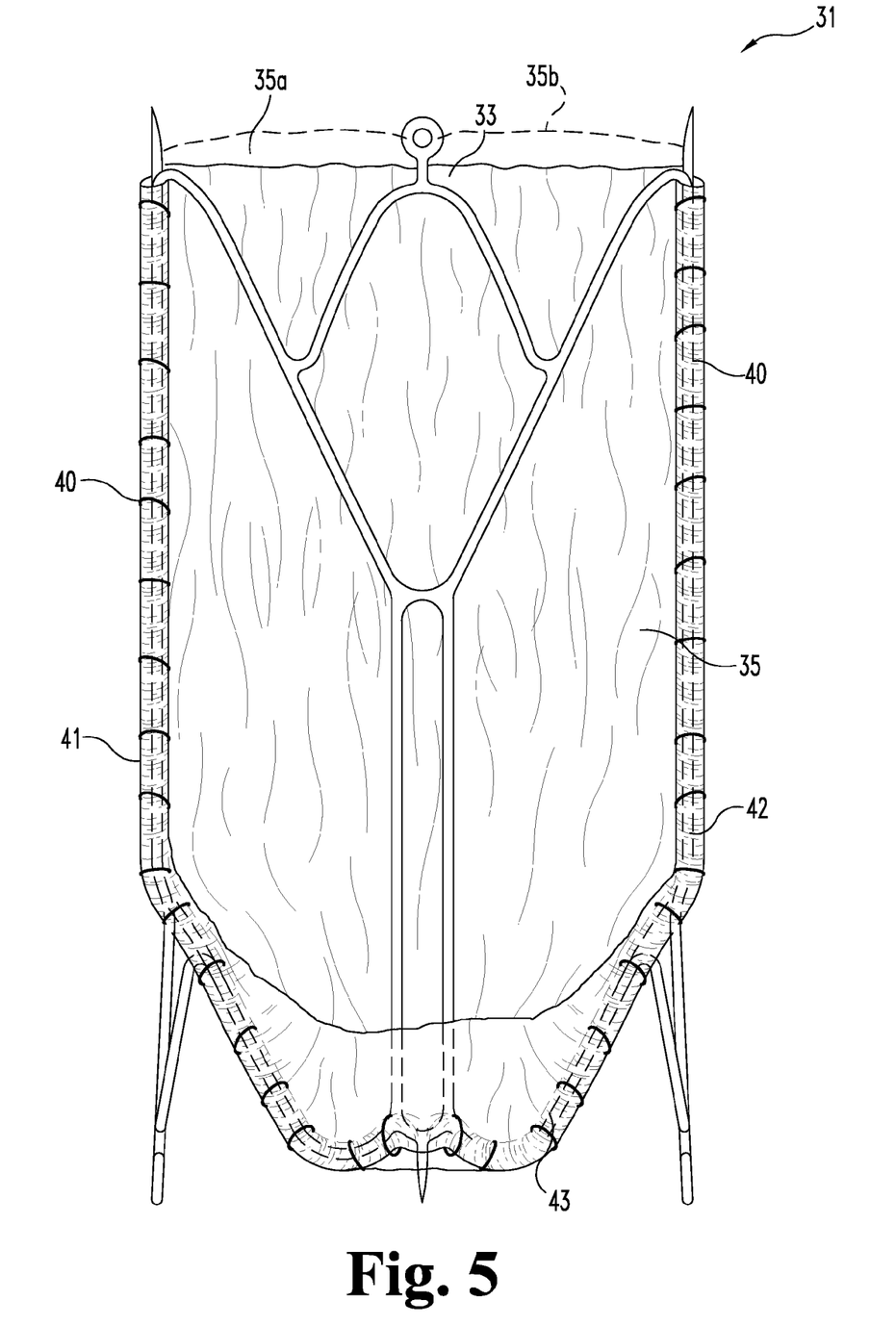
FIG. 5 provides a right side view of the prosthetic valve device depicted in FIG. 3.

With reference now to FIGS. 3-5, depicted are various side views of a prosthetic valve device 31 of the invention. A processed ECM material of the invention is attached to a frame element 33 and provides two leaflets 34 and 35 in a configuration for implantation in a patient. In particular, FIG. 3 provides a side view of prosthetic valve device 31 taken in a direction parallel to the coapting upper edges 34a and 35a of leaflets 34 and 35. FIG. 4 provides a view of the device 31 depicted in FIG. 3 taken from the left side. FIG. 5 provides a view of the device 31 depicted in FIG. 3 taken from the right side. Device 31 is particularly well suited for vascular applications, such as implantation into a vascular passage of a patient.

As can be seen from FIGS. 3-5, leaflets 34 and 35 include respective free edges 34a and 35a for coaptation with one another and respective fixed edges 36 and 40 that will each be forced against the wall of a vascular vessel upon implantation of device 31 in a path that partially circumscribes the vessel wall so as to each form a blood-capturing element. In the device 31 illustrated, the path of leaflet edge contact with the vessel wall includes substantial portions that extend essentially longitudinal along the vessel wall that connect to a cup-forming portion that extends both longitudinally along the vessel wall and circumferentially around the vessel wall. In particular, the fixed edge 36 of leaflet 34 includes opposite longitudinally-extending portions 37 and 38 each extending to an opposite side of a cup-forming portion 39. Correspondingly, the fixed edge 40 of leaflet 35 includes opposite longitudinally-extending portions 41 and 42 each extending to an opposite side of cup-forming portion 43.

The amount of contacting or coapting leaflet area can be expressed in a number of different ways. The length of coaptation (e.g., LOC) in the original configuration for implant is desirably at least about 2 mm and may be as much as about 50 mm or more depending on the configuration of the valve prosthesis. In certain embodiments of the invention, the length of coaptation can be within the range of about 5 to about 30 mm, more typically about 5 to about 15 mm, in the original configuration for implant. The length of coaptation can represent a substantial percentage of the overall length of the valve prosthesis, for example, at least about 5%, or at least about 10%, of the overall length of the prosthesis. In certain embodiments, the length of coaptation of the leaflets represents 10% to 80% of the length of the overall device, typically about 30% to about 60%, and more typically about 35% to about 55%.

In additional aspects, a long length of coaptation can be provided by orienting the outer leaflet edges substantially longitudinally along the frame in close proximity to one another over a significant distance. Thus, with reference to FIGS. 3-5 for purposes of illustration, outer leaflet edge portion 37 of leaflet 34 is configured to contact along the vessel wall in close proximity to outer leaflet edge portion 41 of leaflet 35 over a significant distance, for example 2 to 50 mm, typically about 5 to about 30 mm, and more typically about 5 to about 15 mm. The same would be true for the leaflet edge portions tracking along the opposite side of the vessel wall (e.g., edge portions 38 and 42, FIGS. 3-5). It is preferred that the leaflet edges remain in close proximity over these distances, for example within about 5 mm, more preferably within about 3 mm, and most preferably within about 1 mm.

It will be understood that this close proximity may involve having leaflet edges track closely with one another along the vessel wall, or may have them being attached along essentially the same path (e.g., both along a single strut of a frame) and thus exhibiting essentially no separation from one another as they pass along the vessel wall.

For the purpose of promoting a further understanding of aspects of the present invention, the following specific examples are provided. It will be understood that these examples are illustrative and not limiting of the present invention.

EXAMPLE 1

This example describes the preparation of an one processed ECM material of the invention.

Porcine small intestines were received from a packing plant and were sectioned and split open to reveal their inner portions. After initial cleaning to remove the contents contained within the intestines, each intestine was mechanically abraded on each side to remove mucosa and serosa layers and to isolate a primarily connective tissue layer including the submucosa for further processing. The submucosal layer was treated in a 1:10 (wt:vol) 0.1% sodium dodecyl sulfate (SDS) solution for one hour at 37° C. followed by treatment in a 1:10 (wt:vol) 89 mM tris, borate, ethylene diamine tetraacetic acid (TBE) solution for one hour at 37° C. After these initial treatments, the submucosa was rinsed with 1:10 (wt:vol) high purity water for 5 minutes at ambient temperature. This rinsing step was repeated a second time before treating the submucosa in a 1:5 (wt:vol) 100% isopropyl alcohol (IPA) solution for 30 minutes at ambient temperature. This IPA treatment step was repeated a second time followed by rinsing the submucosa twice as described above. The submucosa was then treated in a 1:10 (wt:vol) 0.2% PAA/5% specially denatured alcohol solution for two hours at ambient temperature. Finally, the submucosa was rinsed in 1:10 (wt:vol) high purity water for 5 minutes at ambient temperature. This rinsing step was repeated for a total of 4 rinses before testing the submucosa for SDS residues. SDS content was measured by using a detergent detection kit (Chemetrics), which indicated that over 97% of the initial detergent was removed. The resulting submucosal tissue was used in the examples that follow.

EXAMPLE 2

This example demonstrates an improved reduction in lipid content using the process described in Example 1 as compared to another process for preparing a submucosal ECM material.

Ten lots of split porcine small intestine were obtained and split into two approximately equal groups. One group was processed as described in Example 1 of U.S. Pat. No. 6,206,931 (hereinafter referred to as the "control group"). Briefly, raw intestine was first treated with peracetic acid followed by mechanically abrading each side to isolate the submucosal tissue layer and rinsing to remove chemical residues. The second group was prepared as described above in Example 1 (hereinafter referred to as the "test group").

Each lot of material was used to make three 4-layer lyophilized sheets by superimposing four of the submucosal layers (wet) and lyophilizing the resultant stack. The 4-layer sheets were sterilized using a low-temperature ethylene oxide cycle. From each sheet, a 1 cm×1 cm sample was cut for lipid content analysis. Three samples were analyzed per group per lot (3 samples×10 lots) for a total of 30 samples for each group. Each sample was weighed (initial weight) and then treated with a solution of 100% ethanol for 24 hours followed by a solution of acetone for 24 hours to extract lipids. Samples were subsequently dried for approximately 48 hours and weighed (final weight). Lipid content was calculated by the initial weight minus the final weight divided by the initial weight.

Distribution analysis was performed to determine which distribution (normal, log-normal, Weibull, or gamma) best fit each set of data. Distribution analysis indicated that the lipid content of the control group best fit the log-normal distribution, which corresponds to an average lipid content of 8.06+/−5.59%. Distribution analysis indicated that the lipid content of the test group best fit the Weibull distribution, which corresponds to an average lipid content of 2.51+/−2.51%.

A p-value of $1.08\times10^{-5}$ was achieved using an unpaired t-test on all of the samples. A p-value of $6.2\times10^{-5}$ was achieved using a pairwise t-test to compare the lot matched control group results with the corresponding test group results. Both p-values are less than 0.05, indicating that there is a statistically significant decrease in the lipid content of the test material as compared to the control material.

EXAMPLE 3

This example demonstrates an improved reduction in IgA content using the process described in Example 1.

Ten lots of split porcine small intestine were obtained and split into two approximately equal groups. One group was processed as described in Example 1 of U.S. Pat. No. 6,206,931 (hereinafter referred to as the "control group"). Briefly, raw intestine was first treated with peracetic acid followed by abrading on each side to isolate a submucosal tissue layer and rinsing to remove chemical residues. The second group was prepared as described above in Example 1 (hereinafter referred to as the "test group").

Each lot of material was made into three, 4-layer lyophilized sheets by superimposing four of the submucosal layers (wet) and lyophilizing the resultant stack. The 4-layer sheets were sterilized using a low-temperature ethylene oxide cycle. From each sheet, a 1 cm×1 cm sample was cut for immunoglobulin A (IgA) content analysis. Three samples were analyzed per group per lot (3 samples×10 lots) for a total of 30 samples for each group. Each sample was weighed (initial weight), placed in a 1.5 mL centrifuge tube, and ground for 90 seconds in 400 µl of phosphate buffered saline (PBS). Samples were subsequently centrifuged, and the supernatant was isolated and diluted 1:5 with sterile PBS. These diluted samples were assayed for IgA content testing by ELISA using a kit from Bethyl Laboratories, Bethyl, Tex. IgA weight content was calculated by dividing the test group IgA content by the initial weight of the control group.

Distribution analysis was performed to determine which distribution (normal, log-normal, Weibull, or gamma) best fit each set of data. Distribution analysis indicated that the control group IgA content best fit the normal distribution, which corresponds to an average IgA content of 50.4+/−27.7 µg/g. One of the test group samples tested at 1.54 µg/g while the all of the other test groups samples tested at 0 µg/g. Distribution analysis was therefore not performed for the test group since the distribution was essentially a single point.

A p-value of $1.7\times10^{-13}$ was achieved using an unpaired t-test on all of the samples. A p-value of $1.88\times10^{-4}$ was achieved using a pairwise t-test to compare the lot matched control group results with the corresponding test group results. Both p-values are less than 0.05, indicating that there is a statistically significant decrease in the IgA content of the material of the test group as compared to the control group.

EXAMPLE 4

This example demonstrates an improved reduction in the number of nuclei using the process described in Example 1.

Ten lots of split porcine small intestine were obtained and split into two approximately equal groups. One group was processed as described in Example 1 of U.S. Pat. No. 6,206,931 (hereinafter referred to as the "control group"). Briefly, raw intestine was first treated with peracetic acid followed by abrading each side to isolate a submucosal tissue layer and rinsing to remove chemical residues. The second group was prepared as described above in Example 1 (hereinafter referred to as the "test group").

A sample from each lot in each group was cut and stained with Hoechst 33258 for identifying nuclei. Three images of the nuclei in each sample were obtained from random locations using an Olympus fluorescence microscope with an ultraviolet filter. Images were taken at a total magnification of 200× by the Spot Insight digital camera and acquired through Spot RT computer software. These images represent a total area of 0.263 $mm^2$. Three independent analyzers counted nuclei for each image acquired. The number of nuclei per image was taken as the average of these 3 counts.

Distribution analysis was performed to determine which distribution (normal, log-normal, Weibull, or gamma) best fit each set of data. Distribution analysis indicated that the control group nuclei counts best fit the Weibull distribution, which corresponds to average nuclei per field for the control group of 473+/−193 nuclei. Distribution analysis indicated that the test group nuclei counts best fit the gamma distribution, which corresponds to average nuclei per field for the test group were 26.7+/−36.1 nuclei.

A p-value of $1.66 \times 10^{-6}$ was achieved using a pairwise t-test to compare the lot matched control group results with the corresponding test group results. The p-value is less than 0.05, indicating that there is a statistically significant decrease in the nuclei content of the test material as compared to the control material.

EXAMPLE 5

This example demonstrates that a processed ECM material as described in Example 1 retains native FGF-2.

Ten lots of raw porcine small intestine were obtained and processed according to Example 1. Each lot of material was made into three, 4-layer lyophilized sheets as described in Example 2 above and sterilized using a low-temperature ethylene oxide cycle. From each sheet, a 1 cm×1 cm sample was cut for FGF-2 content analysis. Three samples were analyzed per lot (3 samples×10 lots) for a total of 30 samples. Each sample was weighed (initial weight), placed into a 1.5 mL centrifuge tube, and ground 3×30 seconds in 400 µl of phosphate buffered saline (PBS). Samples were subsequently centrifuged, and the supernatant was isolated and diluted 1:5 with sterile PBS. These diluted samples were assayed in duplicate for FGF-2 content using R&D Systems FGF-2 ELISA kits. FGF-2 weight content was calculated by dividing the FGF-2 content as determined by ELISA by the initial weight of the sample.

Distribution analysis was performed to determine which distribution (normal, log-normal, Weibull, or gamma) best fit each set of data. Distribution analysis indicated that the FGF-2 content best fit the normal distribution, which corresponds to a mean FGF-content value of 25.0 ng/g+/−12.9 ng/g.

EXAMPLE 6

This example demonstrates that a processed ECM material as described in Example 1 retains native hyaluronic acid (HA).

Ten lots of raw porcine small intestine were obtained and processed according to Example 1. Each lot of material was made into three, 4-layer lyophilized sheets as described in Example 2 above and sterilized using a low-temperature ethylene oxide cycle. From each sheet, a 1 cm×1 cm sample was cut for hyaluronic acid (HA) content analysis. Three samples were analyzed per lot (3 samples×10 lots) for a total of 30 samples. Each sample was weighed (initial weight), placed into a 1.5 mL centrifuge tube, and digested with 50 µl Proteinase K in 450 µl of phosphate buffered saline (PBS) at 56° C. for 45 minutes. Samples were subsequently centrifuged and the supernatant was isolated and diluted 1:40 with sterile PBS. These diluted samples were assayed in duplicate for HA content by ELISA using a kit from Corgenics, Westminster, Colo. HA weight content was calculated by dividing the HA content as determined by ELISA by the initial weight of the sample.

Distribution analysis was performed to determined which distribution (normal, log-normal, Weibull, or gamma) best fit each set of data. Distribution analysis indicated that the test sample HA content best fit the log-normal distribution, which corresponds to an average HA content for the test sample of 303+/−209 µg/g.

EXAMPLE 7

This example demonstrates that a processed ECM material as described in Example 1 retains native sulfated glycosaminoglycans (sGAGs).

Ten lots of raw porcine small intestine were obtained and processed according to Example 1. Each lot of material was made into three, 4-layer lyophilized sheets as in Example 2 above and sterilized using a low-temperature ethylene oxide cycle. From each sheet, a 1 cm×1 cm sample was cut for s(GAG) analysis. Three samples were analyzed per lot (3 samples×10 lots) for a total of 30 samples. Each sample was weighed (initial weight), placed into a 1.5 mL centrifuge tube, and digested with 50 µl Proteinase K in 450 µl of phosphate buffered saline (PBS) at 56° C. for 45 minutes. All samples were vortexed for 5 seconds followed by the addition of 1.0 mL of Blyscan dye reagent. Absorbance readings were taken with a spectrophotometer in triplicate from each sample at 685 nm, and sGAG concentration was calculated from a heparin standard curve. sGAG weight content was calculated by dividing the s(GAG) content as determined by the absorbance readings by the total weight of sample.

Distribution analysis was performed to determine which distribution (normal, log-normal, Weibull, or gamma) best fit each set of data. Distribution analysis indicated that the sGAG content best fit the normal distribution, which corresponds to a mean value of s(GAG) content of 7588 µg/g+/−6505 µg/g.

EXAMPLE 8

This example demonstrates the diaphragmatic burst force of the ECM material that has been processed according to Example 1 as compared to another process.

Ten lots of split porcine small intestine were obtained and split into two approximately equal groups. One group was processed as described in U.S. Pat. No. 6,206,931 (hereinafter referred to as the "control group"). Briefly, raw intestine was first treated with peracetic acid followed by abrading on both sides to isolate a submucosal tissue layer and rinsing to remove chemical residues. The second group was prepared as described above in Example 1 (hereinafter referred to as the "test group").

Each lot was made into three, 4-layer lyophilized sheets as described in Example 2 above or three, 8-layer vacuum pressed sheets by overlapping eight wetted submucosal layers and vacuum-pressing the construct. These sheets were sterilized using a low temperature ethylene oxide cycle. From each sheet, a 2.5 inch×2.5 inch sample was cut for diaphragmatic burst force testing. Three samples were analyzed per lot for the 4-layer lyophilized groups (3 samples×9 lots) for a total of 27 samples. Three samples were analyzed per lot for the 8-layer vacuum pressed groups (3 samples×10 lots) for a total of 30 samples. Each sample was rehydrated in phosphate buffered saline (PBS) for at least 15 minutes prior to testing. The diaphragmatic burst force was measured before breaking using the Mullen's burst force tester.

Distribution analysis was performed to determined which distribution (normal, log-normal, Weibull, or gamma) best fit each set of data. Distribution analysis indicated that the control 4-layer lyophilized burst force best fit the Weibull distribution, which corresponds to an average burst force of 359+/−98 kPa. Distribution analysis indicated that the test 4-layer lyophilized diaphragmatic burst force best fit the log-normal distribution, which corresponds to an average burst force of 378+/−79 kPa. The average difference in diaphragmatic burst force between the two groups was 5.3%. A p-value of 0.458 was achieved using an unpaired t-test on all of the samples. A p-value of 0.060 was achieved using a paired t-test to compare the lot matched control group results with the corresponding test group results. Both of these p-values are greater than 0.05, indicating that there was not a statistically significant decrease in the diaphragmatic burst force of a 4-layer lyophilized material of the present invention as compared to a 4-layer lyophilized material prepared by a currently used process.

With respect to the 8-layer vacuum pressed materials, distribution analysis indicated that the control 8-layer vacuum pressed burst force best fit the log-normal distribution, which corresponds to an average burst force of 915+/−234 kPa. Distribution analysis indicated that the test 8-layer vacuum pressed burst force best fit the log-normal distribution, which corresponds to an average burst force of 872+/−269 kPa. The average difference in burst force between the two groups was 4.8%. A p-value of 0.516 was achieved using an unpaired t-test on all of the samples. A p-value of 0.217 was achieved using a paired t-test to compare the lot matched control group results with the corresponding test group results. Both of these p-values are greater than 0.05, indicating that there was not a statistically significant decrease in the burst force of the 8-layer vacuum-pressed test material as compared to the 8-layer vacuum-pressed control material.

EXAMPLE 9

This example demonstrates the suture retention strength of the ECM material that has been processed according to Example 1 as compared to another process for preparing a sterilized, isolated submucosa tissue.

Ten lots of split porcine small intestine were obtained and split into two approximately equal groups. One group was processed as described in U.S. Pat. No. 6,206,931 (hereinafter referred to as the "control group"). Briefly, raw intestine was first treated with peracetic acid followed by abrading both sides to isolate a submucosal tissue layer and rinsing to remove chemical residues. The second group was prepared as described above in Example 1 (hereinafter referred to as the "test group").

Each lot was made into three, 4-layer lyophilized sheets or three, 8-layer vacuum pressed sheets as described in Example 8. These sheets were sterilized using a low temperature ethylene oxide cycle. From each sheet, a 1 cm×3 cm sample was cut for suture retention strength testing. Three samples were analyzed per group per lot (3 samples×10 lots) for a total of 30 samples for each group. The 4-layer lyophilized material was cut in the two primary directions, longitudinal and transverse, while the 8-layer material was only cut in one direction since this material has no primary direction due to the orthogonal overlapping of the layers. Each sample was rehydrated in phosphate buffered saline (PBS) for at least 15 minutes prior to testing. A 302/304 stainless steel wire, equal in size to the 5-0 sutures used clinically, was passed through one end of each test article, with a bite depth of 2 mm, and was attached to the movable jaw of the tensile testing machine. The other end of each test article was gripped in the stationary jaw of the tensile testing machine and the wire was pulled upward at a constant rate of 150 mm/min. The maximum force, extension at break, and failure mode were recorded for each sample. All of the test samples (180/180, 100%) failed as a result of the steel wire pulling out of the SIS material. In all instances, the steel wire remained intact and the SIS material failed.

The results of the tests are as follows (mean +/−standard deviation): 8-layer vacuum pressed control group=12.22+/−2.68 N, 8-layer vacuum pressed test group=12.77+/−1.81 N (p=0.3714); 4-layer lyophilized control group transverse=7.58+/−1.68 N, 4-layer lyophilized test group transverse=7.99+/−1.90 N (p=0.3801); 4-layer lyophilized control group longitudinal=6.19+/−1.46 N, 4-layer lyophilized test group longitudinal=6.14+/−1.41 N (p=0.8929). Goodness of fit tests for normality on the data sets showed that none of the data sets had any significant departures from a normal distribution. Therefore, two sample t-tests (control versus test groups) were run on each group of data (8-layer vacuum pressed, 4-layer lyophilized transverse, and 4-layer lyophilized longitudinal). All p-values were greater than 0.3714, indicating that there was no statistically significant decrease in suture retention strength in the test materials as compared to the control materials.

EXAMPLE 10

This example demonstrates the tensile strength of the ECM material that has been processed according to Example 1 as compared to another process for preparing a sterilized, isolated submucosal tissue.

Ten lots of split porcine small intestine were obtained and split into two approximately equal groups. One group was processed as described in U.S. Pat. No. 6,206,931 (hereinafter referred to as the "control group"). Briefly, raw intestine was first treated with peracetic acid followed by abrading on both sides to isolate a submucosal tissue layer and rinsing to remove chemical residues. The second group was prepared as described above in Example 1 (hereinafter referred to as the "test group").

Each lot was made into three, 4-layer lyophilized sheets or three, 8-layered vacuum pressed sheets as in Example 8. These sheets were sterilized using a low temperature ethylene oxide cycle. From each sheet, a "dog bone" shaped sample was cut for tensile testing. Three samples were analyzed per group per lot (3 samples×10 lots) for a total of 30 samples for each group. The 4-layer lyophilized material was cut in the two primary directions, longitudinal and transverse, while the 8-layer material was only cut in one direction. Each sample was rehydrated in phosphate buffered saline (PBS) and tested for the ultimate tensile force (UTF) before breaking using the Instron at a deformation rate of 100 mm/minute.

Distribution analysis was performed to determine which distribution (normal, log-normal, Weibull, or gamma) best fit each set of data. Distribution analysis indicated that the control 4-layer lyophilized in the longitudinal direction UTF best fit the log-normal distribution, which corresponds to an average UTF of 3.72+/−1.05 lbs. Distribution analysis indicated that the test material 4-layer lyophilized in the longitudinal direction UTF best fit the normal distribution, which corresponds to an average UTF of 2.92+/−0.88 lbs. The average difference in UTF between these two groups was 21%. A p-value of $3.6 \times 10^{-3}$ was achieved using an unpaired t-test on all of the samples. A p-value of $3.4 \times 10^{-3}$ was achieved using a paired t-test to compare the lot matched control group results with the corresponding test group results. Both of these p-values are less than 0.05, indicating that there was a statistically significant decrease in UTF in the longitudinal direction of the 4-layer lyophilized test material as compared to the 4-layered lyophilized control material.

Similarly, distribution analysis indicated that the control 4-layer lyophilized in the transverse direction UTF best fit the log-normal distribution, which corresponds to an average UTF of 3.2+/−0.96 lbs. Distribution analysis indicated that the test material 4-layer lyophilized in the longitudinal direction UTF best fit the log-normal distribution, which corresponds to an average UTF of 2.48+/−0.90 lbs. The average difference in UTF between these two groups was 22%. A p-value of $7.1 \times 10^{-3}$ was achieved using an unpaired t-test on all of the samples. A p-value of $5.11 \times 10^{-2}$ was achieved using a paired t-test to compare the control group results with the corresponding test group results. Both of these p-values are less than 0.05, indicating that there was a statistically significant decrease in UTF in the transverse direction of the 4-layer lyophilized test material as compared to the 4-layered lyophilized control material.

With respect to the 8-layer material, distribution analysis indicated that the control 8-layer vacuum pressed UTF best fit the Weibull distribution, which corresponds to an average UTF of 10.78+/−3.35 lbs. Distribution analysis indicated that the test material 8-layer vacuum pressed UTF best fit the normal distribution, which corresponds to an average UTF of 7.46+/−2.45 lbs. The average difference in UTF between these two groups was 31%. A p-value of $6.4 \times 10^{-5}$ was achieved using an unpaired t-test on all of the samples. A p-value $9.9 \times 10^{-7}$ was achieved using a paired t-test to compare the lot matched control group results with the corresponding test group results. Both of these p-values are less than 0.05, indicating that there was a statistically significant decrease in UTF of the 8-layer vacuum-pressed test material as compared to the 8-layered vacuum-pressed control material.

EXAMPLE 11

This example demonstrates that the processed ECM material of Example 1 exhibits angiogenic character.

A disc for implantation was formed of porcine small intestinal submucosa (SIS) processed in the following ways: Control lyophilized (prepared as described in Example 1 of U.S. Pat. No. 6,206,931), control vacuum pressed (prepared as described in Example 1 of U.S. Pat. No. 6,206,931), test lyophilized (prepared as described in Example 1), test vacuum pressed (prepared as described in Example 1), and a wound care product Promogran® (PR). Control and test discs were sterilized with a low temperature ethylene oxide cycle prior to implantation. The PR product was received sterile and processed aseptically. Each disc was implanted into the subcutaneous dorsi of a mouse for 3 weeks. After 3 weeks, each disc was probed for capillary formation. Angiogenesis was measured qualitatively using fluorescence microangiography, a method of imaging intact, functional microvasculature. Vessel capacity, as a measure of angiogenesis, was determined using vascular perfusion of fluorescent microspheres, followed by fluorescence extraction from the implants using xylenes, and subsequent quantitation with a fluorescence plate reader. Lastly, implants were examined histologically by thin sectioning and H&E staining to illustrate cellular ingrowth.

Fluorescence microangiography indicated that all discs supported angiogenesis. The test lyophilized disc had similar results to the control lyophilized disc. The test vacuum pressed disc performed superior to the control vacuum pressed disc. The PR disc had significantly less vascular growth with only one area for the two samples investigated having any ingrowth. Vessel capacity results for the PR disc were significantly less than the control. There was no statistical difference for any of the other discs tested. Histology confirmed the microangiography findings. The lyophilized control disc and the lyophilized test disc had significant fibrovascular ingrowth. The vacuum pressed control disc had only minor penetration. The vacuum pressed test disc had more cellular ingrowth, mirroring the results of the microangiography, but still had signs of unincorporated SIS near the edge likely due to the dense nature of this material. Very little cellular ingrowth was evident in the PR disc, suggesting very little evidence of functional remodeling.

EXAMPLE 12

This example provides a comparison of the processed ECM of Example 1 with another processed ECM when used in a rat abdominal wall repair model.

Ten lots of split porcine small intestine were obtained and split into two approximately equal groups. One group was processed as described in Example 2 of U.S. Pat. No. 6,206,931 (hereinafter referred to as the "control group"). Briefly, raw intestine was first treated with peracetic acid followed by abrading on both sides to isolate a submucosal tissue layer and rinsing. The second group was prepared as described above in Example 1 (hereinafter referred to as the "test group").

Each lot of material was made into a 4-layer vacuum pressed test implant or a 4-layer vacuum pressed control implant. A 2 cm×2 cm defect was created in the rat abdominal fascia and each implant was implanted to provide the repair. After two, four, or eight weeks, the rats were sacrificed and implants were removed. A dog-bone shaped piece was cut from each implant and tested for mechanical strength.

The test implants were compared against their control counterparts at each time point for mechanical strength at failure. In addition, at explant, any complications were noted. Complications tallied included infection, abdominal adhesion formation, and seroma formation. At each time point, the test implant had similar UTF to failure compared to the corresponding control implant. The test implant elicited less negative reaction from the host. Specifically, only one seroma was noted in the test material at all points, while 5 seromas were seen in the control implant. Lastly, the histology indicated that the test implant remodeled as well as, if not better than, the control implant.

EXAMPLE 13

This example describes the preparation of another processed ECM material of the invention.

Porcine small intestines were received from a packing plant and were sectioned and split open to reveal their inner portions. After initial cleaning to remove the contents contained within the intestines, each intestine was mechanically abraded on each side to remove mucosa and serosa layers and to isolate a primarily connective tissue layer including the submucosa for further processing. The submucosal layer was treated in a 1:5 (wt:vol) 99% isopropyl alcohol (IPA) solution for 30 minutes at ambient temperature. This IPA treatment step was repeated a second time followed by rinsing the submucosa twice with tap water. The submucosa was then treated in a 1:10 (wt:vol) 0.1% sodium dodecyl sulfate (SDS) heated solution for one hour at 37° C. followed by treatment in a 1:10 (wt:vol) 89 mM tris, borate, ethylene diamine tetraacetic acid (TBE) heated solution for one hour at 37° C. The treated submucosa was then rinsed twice with tap water. After rinsing, the submucosa was treated in a 1:10 (wt:vol) 0.2% PAA/5% specially denatured alcohol solution for two hours at ambient temperature. After these treatment steps, the submucosa was rinsed with 1:10 (wt:vol) high purity water for 5 minutes at ambient temperature. This rinsing step was repeated for a total of 4 rinses before testing and release. The rinse water was tested for pH, conductivity and PAA content. A sample of submucosa was tested for bioburden after disinfection as well as for physical attributes.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A medical graft material, comprising:
   a sterile, decellularized extracellular matrix (ECM) material including collagen and non-collagen components, wherein said non-collagen components include:
   (i) native IgA at a level of no greater than about 20 µg/g;
   (ii) native lipids at a level of no greater than about 4% by weight;
   (iii) native FGF-2 at a level of at least about 10 ng/g;
   (iv) native hyaluronic acid at a level of at least about 50 µg/g; and
   (v) native sulfated glycosaminoglycans at a level of at least about 500 µg/g.

2. The medical graft material of claim 1, wherein said ECM material comprises submucosa.

3. The medical graft material of claim 2, wherein said submucosa is intestinal, urinary bladder or stomach submucosa.

4. The medical graft product of claim 3, wherein said submucosa is small intestinal submucosa (SIS).

5. The medical graft material of claim 1, wherein said ECM material has visible nuclei present at a level less than 200 per 0.263 mm$^2$.

6. The medical graft material of claim 1, wherein the ECM material includes native IgA at a level of no greater than 10 µg/g.

7. The medical graft material of claim 1, wherein the ECM material includes native IgA at a level of no greater than 5 µg/g.

8. The medical graft material of claim 1, wherein the ECM material is essentially free from native IgA.

9. A medical graft material, comprising:
   a sterile, decellularized extracellular matrix (ECM) material including collagen and non-collagen components, wherein said non-collagen components include native IgA at a level of no greater than 20 µg/g and at least one of native FGF-2, native hyaluronic acid, and native glycosaminoglycans.

10. The medical graft material of claim 9, wherein the ECM material includes native IgA at a level of no greater than 15 µg/g.

11. The medical graft material of claim 9, wherein the ECM material includes native IgA at a level of no greater than 10 µg/g.

12. The medical graft material of claim 9, wherein the ECM material includes native IgA at a level of no greater than 5 µg/g.

13. The medical graft material of claim 9, wherein the ECM material is essentially free from native IgA.

14. The medical graft material of claim 9, wherein the ECM material has a lipid content of no greater than about 4%.

15. The medical graft material of claim 9, wherein the ECM material includes a lipid content of no greater than about 3%.

16. The medical graft material of claim 9, wherein the ECM material is formed as one or more of a sheet, a gel, a non-gelled aqueous composition, a powder, or a sponge.

17. The medical graft material of claim 16, wherein said ECM material is formed as a sheet and is lyophilized.

18. The medical graft material of claim 17, wherein the ECM material is formed of at least two ECM layers, and wherein the at least two ECM layers are coupled to one another.

19. The medical graft material of claim 9, wherein said ECM material comprises native FGF-2, native hyaluronic acid, and native glycosaminoglycans.

20. The medical graft product of claim 9, wherein said ECM material comprises submucosa.

21. The medical graft product of claim 20, wherein said submucosa is intestinal, urinary bladder or stomach submucosa.

22. The medical graft product of claim 21, wherein said submucosa is small intestinal submucosa (SIS).

23. The medical graft material of claim 9, wherein said ECM material retains native FGF-2 at a level of at least 10 μg/g and has visible nuclei present at a level less than 200 per 0.263 mm$^2$.

24. The medical graft material of claim 9, wherein said ECM material comprises porcine, bovine, caprine or ovine ECM material.

25. A medical graft material, comprising:
a sterile, decellularized extracellular matrix material exhibiting an angiogenic character and including native IgA at a level of no greater than 20 μg/g.

26. The medical graft material of claim 25, wherein said ECM comprises submucosa.

27. The medical graft material of claim 26, wherein said submucosa is intestinal, urinary bladder or stomach submucosa.

28. The medical graft product of claim 27, wherein said submucosa is small intestinal submucosa (SIS).

29. The medical graft material of claim 25, wherein said extracellular matrix material retains native FGF-2 at a level of at least 10 μg/g and has visible nuclei present at a level less than 200 per 0.263 mm$^2$.

30. The medical graft material of claim 25, wherein said extracellular matrix material retains native FGF-2 at a level of at least about 10 μg/g.

31. The medical graft material of claim 30, wherein said extracellular matrix material has a lipid content of no greater than about 4%.

* * * * *